United States Patent [19]

Ernst et al.

[11] 3,972,327
[45] Aug. 3, 1976

[54] RESPIRATOR

[75] Inventors: Heini Ernst, Witterswil; Albert Guenin, Therwil, both of Switzerland

[73] Assignee: Hoffmann-La Roche Inc., Nutley, N.J.

[22] Filed: Nov. 7, 1974

[21] Appl. No.: 521,801

Related U.S. Application Data

[63] Continuation of Ser. No. 343,779, March 22, 1973, abandoned.

[52] U.S. Cl. ................. 128/145.8; 128/DIG. 17; 137/487.5; 73/194 E
[51] Int. Cl.² .................................... A61M 16/00
[58] Field of Search ............ 128/145, 145.5, 145.6, 128/145.7, 145.8, 188, 142, 142.2, 1 B; 137/486, 487.5; 73/194 E, 205 D, 205 C

[56] References Cited
UNITED STATES PATENTS

| 2,376,348 | 5/1945 | Fox | 128/145.8 |
|---|---|---|---|
| 2,830,580 | 4/1959 | Saklad et al. | 128/145.8 |
| 3,191,596 | 6/1965 | Bird et al. | 128/145.5 |
| 3,357,428 | 12/1967 | Carlson | 128/145.8 |
| 3,584,621 | 6/1971 | Bird | 128/145.8 |
| 3,659,598 | 5/1972 | Peters | 128/145.8 |
| 3,682,166 | 8/1972 | Jacobs | 128/145.8 |
| 3,741,208 | 6/1973 | Jonsson | 128/145.6 |
| 3,756,229 | 9/1973 | Ollivier | 128/145.8 |
| 3,766,914 | 10/1973 | Jacobs | 128/145.8 |
| 3,831,596 | 8/1974 | Cavallo | 128/145.8 |

*Primary Examiner*—Robert W. Michell
*Assistant Examiner*—Henry J. Recla
*Attorney, Agent, or Firm*—Samuel L. Welt; Bernard S. Leon; Mark L. Hopkins

[57] ABSTRACT

A respirator used to replace or assist the respiratory function and automatically regulate the respiration gas flow and pressure during the inspiration phase and expiration phase comprising means for measuring the flow and pressure of respiration gas and providing electrical output signals, valve means including an adjustable valve for controlling the flow and pressure of respiration gas past the measuring means, and electronic regulating means connected with the measuring means and valve means for comparing the electrical signals with predetermined values including standard values and for generating a regulating signal for adjusting the valve means.

30 Claims, 9 Drawing Figures

RESPIRATOR

This is a continuation of application Ser. No. 343,779, filed Mar. 22, 1973, now abandoned.

BACKGROUND OF THE INVENTION

1. Field of the Invention

The invention concerns a respirator and more particularly a respirator in which flow and pressure of the respiration gas are automatically regulated during inspiration and expiration.

2. Description of the Prior Art

Respirators serve to replace or assist the respiratory funciton in patients having deficient or insufficient spontaneous respiration. Further, respirators can be employed for anaesthesia.

The usual respirators are controlled systems, that is their functional operating sequence is governed by predefined input variables. A group of known respirators, encompasses the so-called pressure-controlled systems, wherein respiration gas under pressure is supplied to the patient, with a control valve interrupting the respiration gas supply if a certain predetermined pressure is built up in the line leading to the patient. A further group encompasses the so-called volume-controlled systems, by which a quantity of the respiration gas measured according to volume is supplied to the patient. Both types of respirators have a disadvantage which is fundamentally inherent to all controlled systems; specifically, they can not respond in a compensating manner to variations of the lung mechanics which cannot be predicted.

There have also already been proposed automatically regulated respirators, which are not suitable "however" for various reasons for general, routine-type use in hospitals. One reason is that the measurement of the controlled condition calls for a complicated mechanism which on the one hand is expensive and on the other hand is trouble-prone.

SUMMARY

The present invention is grounded in solving the problem of providing an automatically regulated respirator which is free from the disadvantages of known systems and which is suitable for a wide range of applications because of its simple and inexpensive manufacture.

In accordance with the invention, this is achieved by a respirator with a flow and pressure measuring device disposed directly adjacent the patient connection, to measure the flow and pressure of the respiration gas and convert these parameters into electrical signals, a valve system disposed between the respiration gas source and the flow and pressure measuring device for the control of flow and pressure of the respiration gas during inspiration and expiration, and an electronic regulating unit which forms a regulating circuit together with the measuring device and the valve system to compare the electrical signals with standard values and to generate a correction signal which regulates the valve operation.

DESCRIPTION OF THE PREFERRED EMBODIMENT

Figure 1:
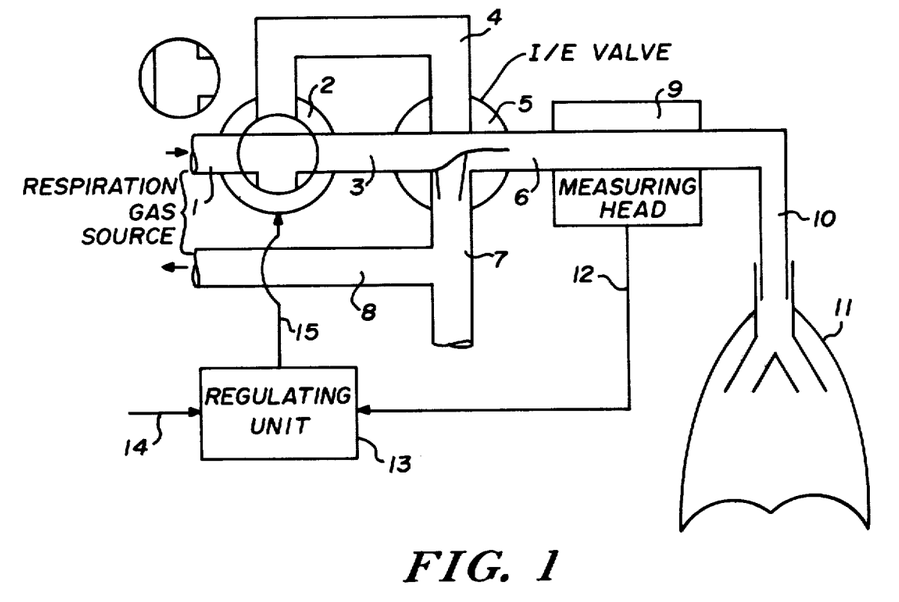
FIG. 1 shows a block diagram of an automatically regulated respirator according to the invention.
Figure 2:
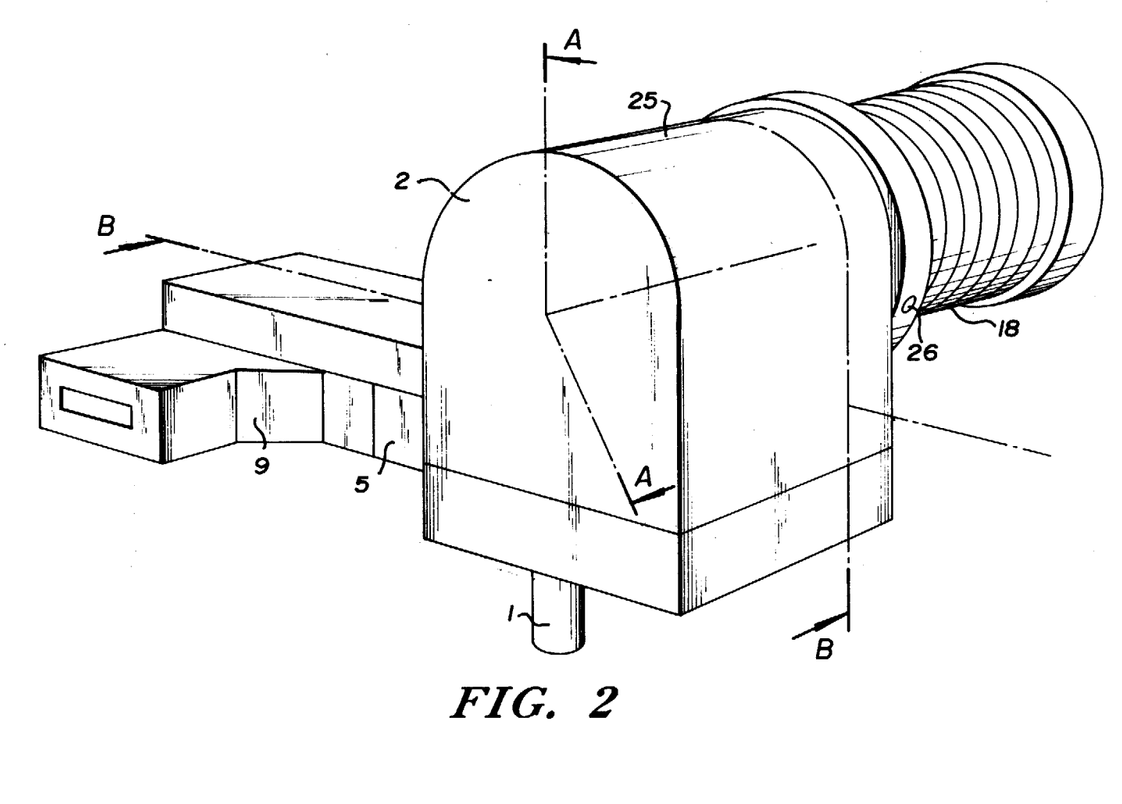
FIG. 2 shows a perspective view of a preferred embodiment of the regulating valve, of the inspiration/expiration valve, and of the measuring head in the assembled state.

The respirator shown in FIG. 1 in block diagram form and partially in FIG. 2 perspectively, serves to supply respiratory gas to a patient designated as 11 from a source (not shown) and to remove such gas from the patient, in a definite rhythm similar to the natural respiration. Either a pressure generator or a central supply system, as is usually installed in larger hospitals, can serve as the respiration gas source. Any desired gas or gas mixture may be employed, for example pure respiration gases such as air, oxygen, or mixtures with narcotic gas such as ether, laughing gas etc. The respiration gas delivered should preferably have a pressure of 1.2 atm. Further, the respiration gas should be adjusted optimally for the requirements of respiration with respect to moisture content and temperature, that is have a temperature of 37°C and be saturated to more than 90% with water. The devices necessary for this purpose are known per se and do not have to be described here.

A line 1 serves for the connection of the respirator to the respiration gas source and leads to a regulating valve 2. The regulating valve 2 serves for the switching between inspiration phase and expiration phase and simultaneously for the control of flow and pressure in the two switching positions. In the inspiration phase, the valve 2 connects the line 1 with a line 3, and, in the expiration phase the valve 2 connects the line 1 with a line 4. In each phase, the magnitude of pressure and flow is controlled by a larger or smaller opening of the valve. The two lines 3 and 4, each lead to an inspiration/expiration valve 5 for convenience hereinafter called I/E valve. Apart from the two lines 3 and 4, also connected to the I/E valve are a patient line 6 and an expiration line 7. Line 7 may either be opened to the atmosphere or for the purpose of recovering the expiration gas may be connected via a line 8 returning to the respiration gas source.

The patient line 6 leads via a measuring head 9 to a tracheal tube 10 for intubation of a patient 11, the measuring head 9 being provided for the measurement of the flow and pressure of the respiration gas signals are generated which are representative of the flow and pressure variation of the respiration gas. An electrical lead 12 serves for the transmission of these signals to an electronic regulating unit 13. Standard signals for the respiration function, are supplied via a line 14 to the regulating unit 13. In the regulating unit 13 the signals from measuring head 9 are processed, compared with the standard signals, and a correction signal is obtained for adjustment of the regulating valve 2. An electrical output lead 15 serves for the transmission of the correction signals to the drive mechanism of the regulating valve 2 for adjustment purposes.

As is especially visible from FIG. 2, the individual elements of the control section, i.e. regulating valve 2, I/E valve 5 and measuring head 9, are assembled into a single unit. This unit is exceptionally compact its dimensions being approximately 15 × 10 × 5 cm.

The regulating valve 2, the I/E valve 5, the measuring head 9, and the regulating unit 13, are individually described below.

Figure 3:
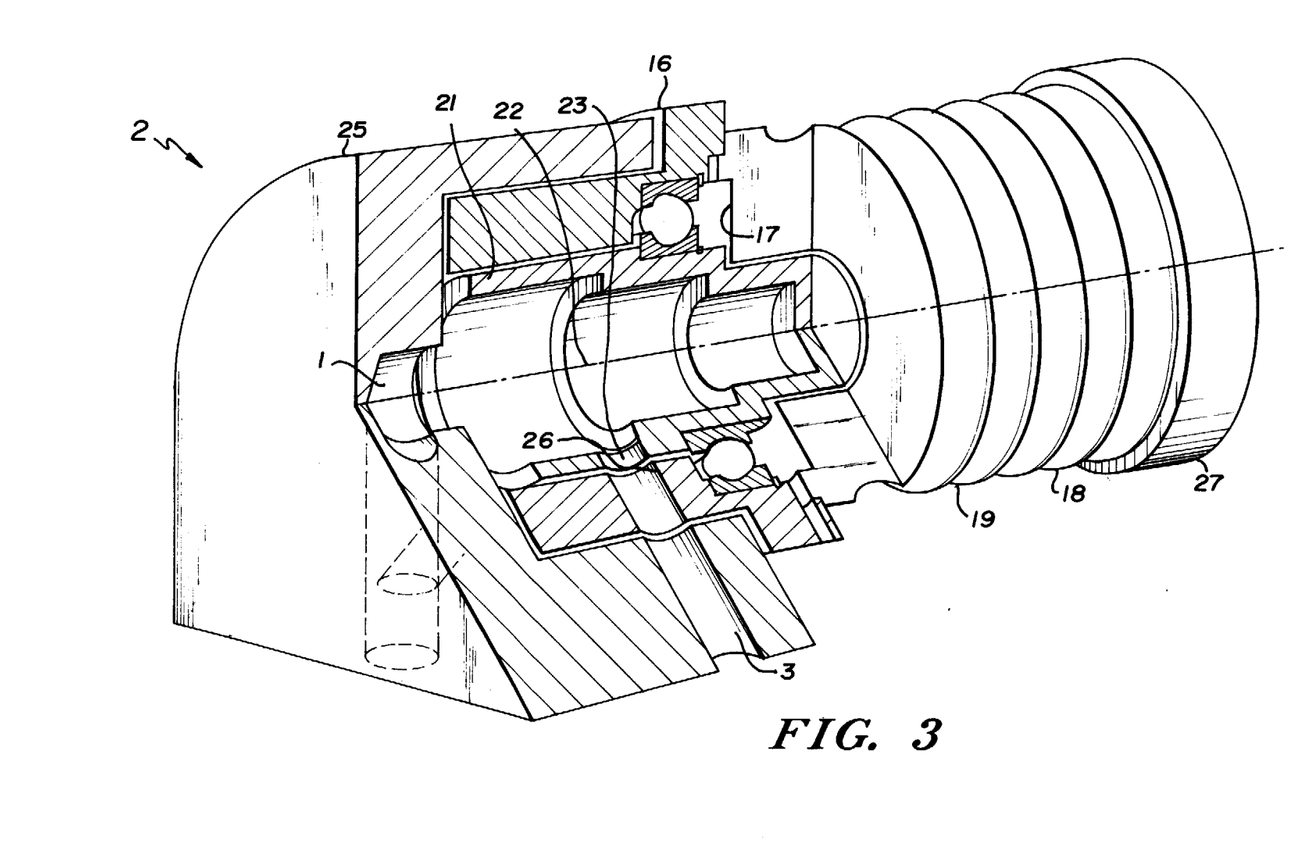
FIG. 3 shows the regulating valve, partially sectioned in the plane A—A of FIG. 2.

The regulating valve 2 as illustrated in cross-section in FIG. 3, includes a substantially hollow-cylindrical housing 16 with an inner bulkhead 17 (running perpendicular to its axis) at one side of which there is attached a commercially available servo-motor 18. The housing side within which the motor 18 is located, is expediently provided with cooling ribs 19. At the side of motor 18, the housing is sealed off with a cover (now shown). The motor-shaft is extended on the one side beyond bulkhead 17 and outwardly on the other side beyond the cover.

The other side of the housing 16 contains the actual valve part. The shaft section is projected within this part of the housing and terminates in the form of a cup-shaped rotor 21. The external diameter of the cylindrical part of the rotor is slightly smaller, for example 0.1 mm, than the internal diameter of the housing. At one position of the cylindrical wall of the rotor 21, an annular boring 22 is provided. The wall of the housing 16 has two borings 23 and 24. The axes of the rotor boring 22 and the two housing borings 23 and 24, lie in a plane perpendicular to the axis of the housing. The distance between the centers of the two housing borings 23 and 24, is greater than the diameter of the boring 22. By appropriate angular position of the rotor, either the rotor boring 22 is brought completely or partially to coincidence with one of the two housing borings 23 or 24, or the housing borings 23 and 24 are closed by the rotor wall.

A part of the housing 16 in which the rotor is seated i.e. the actual valve part, is enclosed by a plastic block 25, which has an inlet line 1 leading to the regulating valve 2 and outlet lines 3 and 4 leading away from the regulating valve. Block 25 is also part of a housing containing the I/E valve 5 and the measuring head 9. The input line 1 extends into the interior of the housing and of the rotor, while the output lines 3 and 4 connect the housing borings 23 and 24 with the corresponding inputs of the I/E valve.

The outer plastic block 25 is readily detachable from the housing 16, i.e. connected for example with clamps or a bayonet connection.

For the venting of the space between the rear of the rotor 21 and the bulkhead 17, there is provided a boring 26 in the housing wall 16.

About the other side of the motor 18, where the shaft 20 is likewise led out, is located a control device 27 for the determination of the angular position of the motor 18 or of the rotor 21. The control device 27 consists essentially of a rotary capacitor with rotatable plates mounted on the shaft 20 and fixed plates which are mounted in insulated manner on the housing and project into the space between the rotatable plates. With application of a voltage between the rotatable and the fixed plates, the angular position of the motor 18 or of the rotor 21 can clearly be determined by the variable capacity. The control device 27 for the determination of the angular position shall not be described in detail as the manufacture of such a device is obvious to one skilled in the art.

The operation of the regulating valve 2 is based on the rotation of the rotor 21 by the servo-motor 18 according to the control signals, so that the rotor boring 22 is selectively brought over one of the housing borings 23 and 24. Respiration gas is delivered under pressure through the inlet line 1. At the beginning of the inspiration phase, the rotor 21 is so rotated that the rotor boring 22 is positioned over the housing boring 23. The respiration gas can consequently flow via the line 3 to the input of the I/E valve. Flow and pressure of the respiration gas can be infinitely controlled between the value zero and a maximum value, through a number of relative displacement positions between the rotor boring 22 and the housing boring 23, thus varying the cross-section of the common aperture.

At the commencement of the expiratory phase the rotor 21 is so rotated that the rotor boring 22 is aligned with the housing boring 24. The gas flows now via the line 4 to the second inlet of the I/E valve, where it is used, as is shown in the following, to generate a negative pressure to assist expiratory respiration. Also in this position flow and pressure of the gas flowing in the line 4 are similarly infinitely controllable between the value zero and a maximum value, by relative displacement of the borings.

It may be desirable to interpose pause intervals between the two phases of a respiration cycle whereby neither respiration gas is supplied to the patient nor is the expiration assisted by production of a negative pressure. In this case, the rotor 21 is so rotated that the rotor boring 22 has no common aperture with either of the two housing borings 23 and 24. To minimize the rotation angle of the rotor, for this case the position between the two housing borings 23 and 24 is expediently chosen. In the construction of the valve 2, no friction washers are provided because these would considerably impair the operating speed. The very small separation between the external surface of the rotor 21 and the internal wall of the housing 16 achieves sufficient sealing tightness to make any resulting loss of respiration gas insignificant. Moreover, the vent boring 26 prevents respiratory gas passing via the motor chamber into the monitoring control device which might otherwise cause disturbances there.

Figure 4:
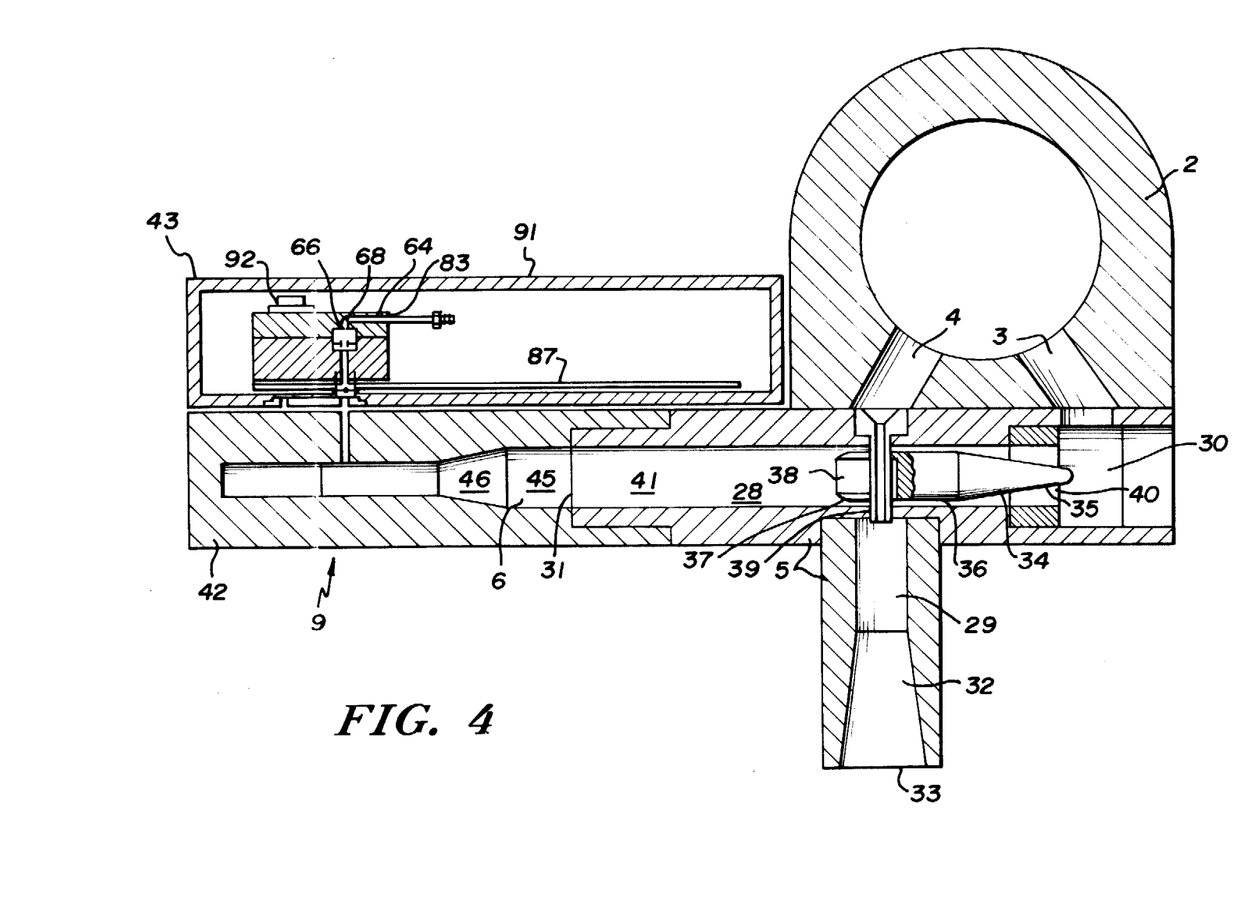
FIG. 4 shows a longitudinal section along the plane B—B of FIG. 2.

As already mentioned, the plastic block 25 which contains the lines 1, 3 and 4 is part of a housing in which the I/E valve is also housed. FIG. 4 shows a section through regulating valve 2, I/E valve 5 and measuring head 9, directed along the longitudinal axis of the I/E valve. The I/E valve has a first or main channel 28 and a second or auxiliary channel 29 running perpendicular thereto and opening approximately in the center thereof. One end 30 of the main channel 28 serves as inlet and communicates directly with the line 3 coming from the regulating valve. The other end 31 of the main channel 28 provides communication between the I/E valve and the line 6 of the measuring head 9. The auxiliary channel 29, in the internal region neighboring the main channel, has firstly a zone of cylindrical form and then widens out conically in an adjacent zone 32. Its end 33 represents the outlet of the I/E valve and serves for the connection to the line 7.

In the main channel 28 there is placed co-axially thereto and in the region of the outlet of the side channel, an elongated bullet-shaped body 34, which is denoted in the following as circumfluous body. With respect to its cross-section the circumfluous body 34 has essentially three zones. In the first zone 35 facing the inlet 30, the body 34 has a conical form with a spherically-rounded end surface, in the central zone 36 a cylindrical form and in the adjacent, third zone 37 again a conical form with spherical rounding at the end. The transition of the cylindrical zone 36 into the conical zone 37 lies in a plane set through the axis of the auxiliary channel, perpendicular to the axis of the main channel.

From the spherically-rounded front end of the circumfluous body 34 facing the measuring head 9, a boring 38 runs first co-axially to the main channel 28 and then, bent at 90°, co-axially to the auxiliary channel 29 up to the part of the exterior surface of the circumfluous body 34 opposite the region of intersection with the auxiliary channel.

A thin tube 39 is installed in corresponding borings of the housing of the I/E valve co-axial to the auxiliary channel and through the circumfluous body. The tube 39 opens into the cylindrical zone of the auxiliary channel 29.

In the zone of the conical part 35 facing the inlet 30, the circumfluous body 34 has a number of radially-arranged vanes or guide vanes 40, which are inclined with respect to planes cutting them through the axis of the main channel at a small angle, for example 6°. The vanes 40 serve on the one hand for the mounting and centering of the circumfluous body 34 and on the other hand, by their inclination thereto, serve for imparting a swirling to the respiration gas flowing through the tube.

The space 41 between the circumfluous body 34 and the line 6 serves as diffuser. Likewise the widened-out part 32 of the side channel 29 serves as diffuser.

In operation, as already described, gas (fixed at an average pressure of ca. 1.2 atm. by the regulating valve 2) is alternately supplied through the lines 3 and 4. In the inspiration phase the gas comes through the inlet 30 into the main channel and flows past the circumfluous body 34. By the reduction of the circumfluous body cross-section in the conical region 35, the flow-rate of the gas increases considerably, that is its pressure energy is converted into kinetic energy. In the zone of the outlet of the auxiliary channel 29, the respiration gas has atmospheric pressure. There does not exist therefore a pressure gradient between the main channel and the auxiliary channel and consequently practically no respiration gas flows through the auxiliary channel during the inspiration phase. The cylindrical part 36 of the circumflous body was selected relatively long so that a laminar flow can develop. In the diffusion region 41 the pressure energy is recovered from the kinetic energy of the gas and a pressure of ca. 1.1 atm. is attained at the end 31 of the main channel.

By means of the vanes 40 a swirling effect is conveyed to the gas coming from the inlet 30 so that a smooth separation of flow is given at the end of the circumfluous body and a separation of flow from the wall of the main channel (which would give an undesired pressure distribution) is avoided.

In the expiration phase the gas expired from the patient, proceeds through the measuring head 9 and the line 6 into the region of the diffuser 41 and through the boring 38 into the auxiliary channel 29. Since the free cross-section remaining between the cylindrical zone 36 of the circumfluous body and the wall of the main channel is smaller than the boring 38 cross-section, practically no expiration gas from end 31 proceeds past the circumfluous body 34 to the input side of the main channel. The boring 38 is of such size that the expiration phase functions well without external assistance.

During the expiration phase the gas, held under pressure by the regulating valve 2, is led in the line 4 to the tube 39 and through this into the auxiliary channel 29. Because of the small cross-section of the tube 39, the gas has a high velocity therein, with which it also discharges into the auxiliary channel 29. This provides an aspirator action with which a negative pressure can be produced on the patient side to assist the expiration phase. Further the suction caused by the respirator action assists to virtually eliminate the passage of any expiration gas past the circumfluous body to the inlet side of the main channel. In the diffusion region 32 of the auxiliary channel the kinetic energy of the gas is again converted into pressure energy so that the gas again has atmospheric pressure at the outlet 33.

The I/E valve has two essential advantages with respect to previously known I/E valves. Since it has no moving parts, no functional disturbances occur due to depositions of liquid drops and solid materials contained in the expiration gas. Practically no obstruction of the channels can occur since in each case they are blown free in the succeeding inspiration phase. The second advantage exists in that the I/E valve can be manufactured completely from plastic because of its simplicity of construction and can be integrated with the manifold block 25 of the regulating valve and the channel of the measuring head 9.

From FIG. 4 the construction of the measuring head 9 is also visible. This consists essentially of two parts, of which the first 42 contains the patient line 6, through which the respiration gas flows during inspiration phase and expiration phase, while the second part 43 contains the actual measuring device. The part 42 of the measuring head containing the patient line 6 consists of a plastic block and is a component of the aforementioned housing also containing the I/E valve and the plastic block 25. The second part 43 containing the measuring device is, on the other hand, mechanically connected with the regulating valve 2, or with the motor 18.

The housing, consisting of the plastic block 25, the I/E valve 5 and the manifold part 42 of the measuring head 9, represents an interchangeable element, which is connected by an easily-detachable mechanism with the fixed parts of the respirator, to which belong the actual valve part of the regulating valve 2, the motor 18 and the control device 27 for the determination of the angular position of the motor 18 as well as the actual measuring part 43 of the measuring head 9. This interchangeable housing is designed as a throw-away part, so that it can be replaced after a single use (i.e. for one patient) and therefore a purification and a sterilization are obviated. For its manufacture a synthetic material is chosen however, which also makes possible a sterilization, so that in a case of emergency in which no new parts are available, the readiness for use of the respirator is ensured.

For the connection of the channel representing the patient line 6 with the actual measuring device 43, channels 44 are provided. These channels 44 open with one end at specific measuring points of the patient line, while their other end opens in each case at the outer limitation of the part 42. If the interchangeable housing is assembled with the fixed parts, the external outlets of the channels 44 lie opposite corresponding openings of the actual measuring device 43 and are there, as is shown in the following, sealed from the surroundings.

Figure 5:
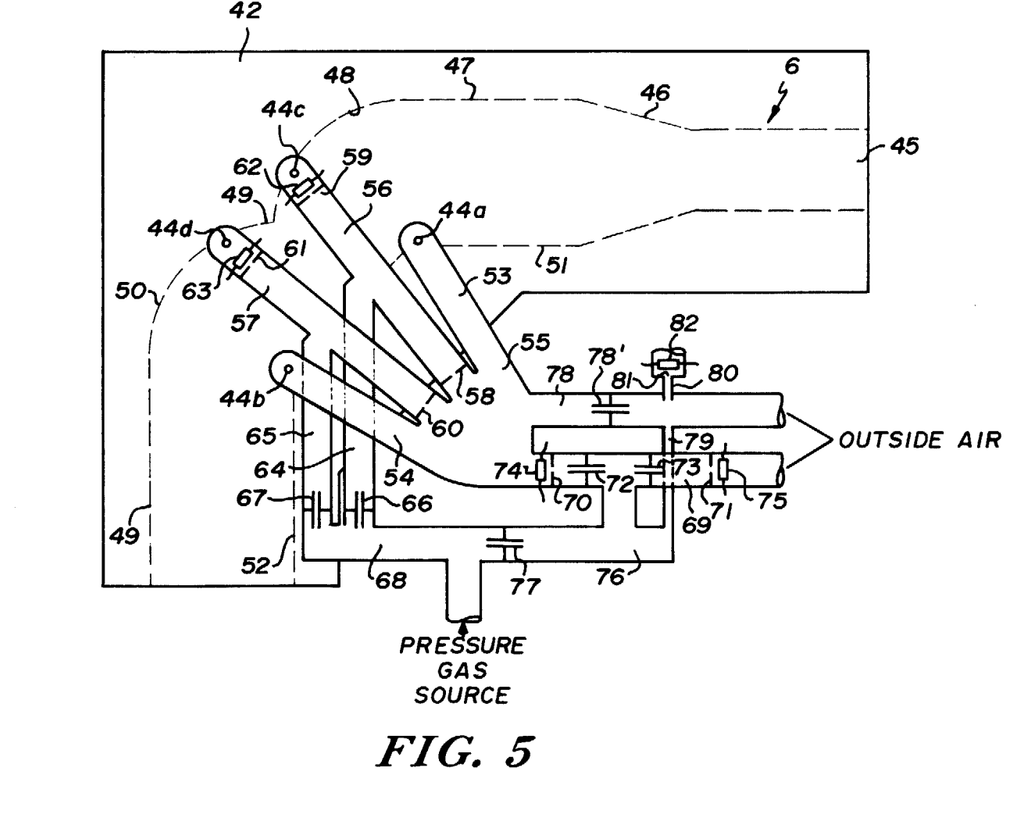
FIG. 5 shows a schematic plan view of the measuring head.

Firstly, the principal of the measuring head is described by way of the FIG. 5 in which there is shown a plan of the interchangeable part 42, and in schematic representation the actual measuring part 43 of the measuring head 9.

Part 42 consists of a substantially L-shaped plastic block with rectangular cross-section. In its interior the patient line 6 runs as a channel inclined substantially at 90°. In its first part 45 connecting to the I/E valve, the channel 6 has an annular cross-section and after a transition region 46 a rectangular cross-section. The outside-bend or outside-curve wall 47 (with respect to the bend of the channel) runs firstly parallel to the axis and breaks away, from a specific plane perpendicular to the axis, into a bend 48 with a radius of curvature equal to the longer side of the rectangular cross-section. In the other leg whose axis runs perpendicular to the aforesaid axis, the outside wall 49 also runs firstly parallel to the axis, to subsequently continue into a bend 50 exactly symmetrical to the bend 48. The inside-bend or inside-curve wall also has two sections 51, 52 parallel to the axes, which lie opposite the axes-parallel sections 47, 49 of the outside wall, while its section opposite the bends 48, 50 runs at an angle of 45°, without curvature however.

For the flow and pressure measurement four measuring points are provided, to which the connection channels 44a, 44b, 44c, 44d lead. As already mentioned, these channels 44 represent the connection between the patient line 6 and the actual measuring device. The two connection channels 44a and 44b open at the points in the patient line, to which the axes-parallel sections 51, 52 of the inside wall bend into the section running at an angle of 45°. The two other connection channels 44c and 44d open at the outside wall of the channel 6 at a position in each case at which the axes of the two side-arms of the channel 6 strike the curved wall-sections 48 and 50.

In the actual measuring part 43 two channels 53, 54 are provided, which on the one hand (if the interchangeable part 42 is assembled) are in connection with the connection channels 44a, 44b and on the other hand are connected with one another via a central cavity 55. From the cavity 55 two further channels 56 and 57 lead to the connection channels 44c, 44d opening at the outside wall of the patient line 6. The two channels 56, 57 have in each case at both of their ends (i.e. thus in the vicinity of the cavity 55 and in the vicinity of their connections to the connection channels 44c, 44d) pneumatic orifice plates 58, 59 or 60, 61. Between the two orifice plates 59, 61 (arranged on the side of the connection channels 44c, 44d) and the two connection channels there is mounted in each case, in the immediate vicinity of the orifice plate opening and as concentrically as possible thereto, a temperature-dependent resistor (abbreviated in the following to thermistor) 62, 63. The connecting leads of the thermistors 62, 63 are led out at the side of the channels and connected with the electronic part of the measuring device (to be described later).

The two channels 56, 57 are connected "moreover" with a channel 64 and 65 each, which in their turn are in connection via pneumatic resistors 66, 67 with a combined channel 68. The channel 68 is connected to a pressure gas source (not shown).

From the central cavity 55 a further channel 69 leads to the outside air. This channel contains pneumatic orifice plates 70, 71 (one mounted in the vicinity of the cavity 55 and one mounted in the vicinity of its outlet to the outside air) and two pneumatic, resistors 72, 73 between these two orifice plates. Between the pneumatic orifice plate 70 and the cavity 55 a thermistor 74 is mounted in the immediate vicinity of the orifice plate opening and between the pneumatic orifice plate 71 and the outside air a thermistor 75 is mounted in the immediate vicinity of the orifice plate opening. The part of the channel 69 lying between the two pneumatic resistors 72, 73 is connected via a connection channel 76 and a further pneumatic resistor 77 with the channel 68.

Finally, another channel 78 leads from the cavity 55 to the outside air. In the channel 78 there opens a narrow connection line 79 (to the connection channel 76) and a likewise narrow passageway 80 (opposite the line 79) in which a thermistor 82 is mounted behind an orifice plate 81 and which opens to the outside air. A pneumatic resistor 78' is mounted in the channel 78.

The connecting leads of the thermistors 74, 75 and 82 are likewise led out at the side of the channels and lead to the electronic part of the measuring device.

The function of the measuring device is as follows: from a pressure gas source a gas stream is supplied via the channel 68, which distributes itself to the individual branches of the device. A part of the gas stream proceeds through the pneumatic resistors 66 and 67 into the channels 64, 65 and further into the channels 56 and 57. Since in the channels 56 and 57 similar processes occur, the description can be limited in the following to one 56 of the two channels. In the channel 56 the gas stream arriving through the channel 64 again splits up into two branches of which one flows through the opening of the orifice plate 58 into the cavity 55, while the other proceeds through the opening of the orifice plate 59 past the thermistor 62 into the connection channel 44c and from there into the patient line 6. These two branch streams serve for the measurement of the inspiratory flow in the patient line 6.

If no gas flows in the patient line 6, the same pressure exists at all measuring points. The two branch streams flowing through the openings of the orifice plates 58 and 59 occur accordingly at the same pressure and remain unchanged for the time being. During the inspiration however the respiration gas coming from the I/E valve flows through the patient line and "bounds" onto the curved part 48 of the outside wall. In this stream a higher pressure exists at the outlet of the connection channel 44c than in the region of the inside wall of the channel (i.e. at the outlets of the connection channels 44a and 44b) and therewith a higher pressure also exists than in the cavity 55. By this pressure difference the two branch streams vary in the channel 56 in a manner such that the stream directed through the opening of the orifice plate 59 becomes smaller and the stream directed through the opening of the orifice plate 58 becomes larger. This variation of the branch stream proceeding through the opening of the orifice plate 59 is measured with the air of the thermistor 62.

For the measurement the impedance of the thermistor is regulated to a constant value. With an equivalent gas stream coming through the orifice plate 59 the thermistor is equivalently cooled, by which means an equilibrium appears in the stationary state. In the non-stationary state, that is if an inspiratory flow exists and therewith the branch stream coming through the opening of the orifice plate 59 varies, the heat conducted by the gas also varies and therewith in turn the power loss of the thermistor 62. The electric current supplied to the thermistor 62 is measured and a variation of the power loss is accordingly determined.

It has been found that the variation of the rates of the two branch streams in the channel 56, and therewith also the heat conduction brought about at the thermistor 62 by one of the two branch streams as well as ultimately also the power loss variation of the thermistor or the signal recording this power loss variation, shows a clear dependence of the variation of the inspiratory flow existing in the patient line 6. Therewith an electric signal recording the flow can be obtained. The flow signal is, for the purpose of regulation, supplied to the electronic circuit (to be described later).

The measurement of the expiratory flow proceeds in the same manner with the aid of the thermistor 63 arranged in the channel 57.

For simplification it has been assumed here that during the inspiration no signal is obtained at the thermistor 63 and during the expiration no signal is obtained at the thermistor 62. Strictly speaking this is not correct, however these undesired signals are considerably smaller than the signals used for the measurement and can be readily eliminated in the subsequent processing.

One part of the gas stream (brought up through the line 68) proceeds via the pneumatic resistor into the channel 76 and is used for the pressure measurement. The stream proceeds into the channel 69 and proceeds here via the two pneumatic resistors 72 and 73 to the orifice plates 70 and 71. If barometric pressure exists in the cavity 55, the gas streams proceeding through the openings of the orifice plates 70 and 71 and therewith the cooling capacity of the thermistors 74 and 75 are of the same magnitude. With a pressure difference between the pressure existing in the cavity 55 and the atmospheric pressure, a difference of the gas streams cooling the thermistors 74 and 75 is also produced, by which means a difference signal can be obtained. It has been found that this difference signal is proportional to the desired pressure difference.

One part of the gas stream proceeding into the channel 76 is led via the line 79 into the channel 78 and serves for the zero adjustment of the pressure signal. Since the channel 78 represents a connection between the cavity 55 and the outside air, a flow is formed in one or the other direction depending on the sign of the pressure difference between the pressure existing in the cavity (denoted as buccal pressure $P_{bucc}$) and the atmospheric pressure. If no pressure difference exists between the cavity 55 and the outside air and therewith no gas flows into the channel 78, this condition corresponding to the desired zero point, the gas arriving through the line 79 proceeds into the passageway 80 and through the opening of the orifice plate 81 to the thermistor 82. Since during the respiration the buccal pressure alternates from time to time between a value lying below the barometric pressure and one lying above the barometric pressure, the desired zero state exists briefly from time to time in the channel 78. In this short time period, a signal is given from the thermistor 82. This signal can moreover be used to adjust the measured pressure signal to zero in every respiration cycle. This device for the zero adjustment saves a frequent manual zero adjustment.

Just as for the obtained pressure signals, a zero adjustment is also necessary for the flow signals, since the zero lines for both signals have a tendency to shift because of various external effects. The zero adjustment of the flow signals is however, as is shown later, electronically undertaken.

Figure 6:
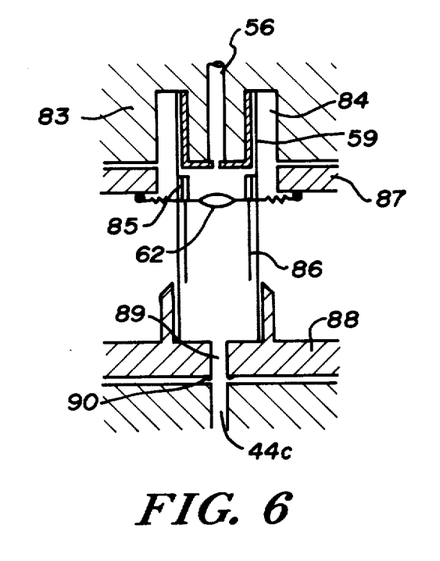
FIG. 6 shows a longitudinal section of a portion of the measuring head in FIG. 4 in enlarged scale.

While in FIG. 5 the actual measuring device for the flow and pressure measurement is shown schematically, from FIG. 4 the actual construction can be seen. All channels as well as the cavity 55 are housed on the inside of one of two parts of a metal block 83 lying flat on one another. They are partially recessed in the separating surfaces between the two parts of the metal block 83, partially composed of borings perpendicular to these separating surfaces. The section resolved in FIG. 4 runs through a section of the channel 68, the pneumatic resistor 66, the channels 64 and 56, the pneumatic orifice plate 59, the thermistor 62 and the channel 44c. For the illustration of the construction a description of the measuring point shown in this section is sufficient, since the other measuring points correspond in principle to the one in question. This measuring point is shown in FIG. 6 in enlarged scale.

The pneumatic resistors are composed for example from metal capillaries which are brought to the desired resistance value by compression at a specific point. They can be pressed into the provided connection borings between the individual channels in a manner known per se. The boring representing a part of the channel 56, opens into the front end of the metal block 83 opposite the interchangeable part of the measuring head 9, that is opposite the connection channel 44c. Concentrically to the outlet of this boring an annular groove or channel 84 is recessed into the front end of the metal block. The internal diameter of this groove is somewhat larger than the diameter of the boring, so that a rim remains. Over this rim is inverted a cylinder-like sleeve 59 closed at one end, which has a concentric aperture in its flat section. This sleeve represents the pneumatic orifice plate. Moreover a further cylindrical sleeve 85 opened at both ends of an electrically insulated material is inserted into the groove. A further sleeve 86 of the same diameter is mounted on the sleeve 85. The thermistor 62 is clamped between the two sleeves 85 and 86. Its connecting wires pass outwards through both sides and are soldered onto a printed circuit board 87. The sleeve 86 passes through the circuit board 87 and is mounted on a rubber plate 88. The rubber plate 88 has an aperture 89 and this aperture has annular encircling sealing washers 90. The whole arrangement is housed in a housing 91, which has a corresponding opening on the side of the interchangeable part 42 in which the rubber plate 88 is installed. In the assembled state the rubber plate is pressed with the sealing washers 90 onto the surface of the interchangeable part 42 such that a sealing from the surroundings results.

For the thermostatical stabilizing of the metal block 83, a power transistor is mounted on its other side. The interspace between the metal block 83 and the wall of the housing 91 is sealed from the surroundings and is in contact with the supply of the gas used for the measurement. Since nitrogen is usually used for the measurement, there is provided therewith a protection from explosion in this space which contains the power transistor 92.

As already mentioned, the regulation of the respirator is effected by the electronic regulating unit 13, which controls the regulating valve 2, by means of both, measured actual values of the flow and pressure and of given standard values. In the present embodiment a flow regulation normally takes place during the inspiration while a pressure regulation takes place during the exspiration. This type of regulation has proved especially expedient for a number of reasons as follows. During the inspiration a specific standard volume of the respiration gas is supplied to the patient. At the commencement of the expiration the final inspiratory pressure is taken as starting value for the pressure regulation and the buccal pressure is brought according to a definite curve to the value zero or barometric pressure. The curves of the flow and pressure variation are presented as standard curves; simultaneously the corresponding actual values are measured and serve for the correction of the standard curves. There has been fixed as an overriding condition that the standard minute volume is adhered to. For this purpose the volume is calculated with the aid of the flow measurement and used for the correction of one or more of the other standard values.

As a further condition it has been intended that during the inspiration the buccal pressure and its increase per unit time must not exceed specific maximum values. If during the flow regulation one of these maximum values is attained in the inspiration, the regulating unit switches to pressure regulation until the flow curve brings about a pressure or pressure increase lying below the maximum values.

Figure 7:
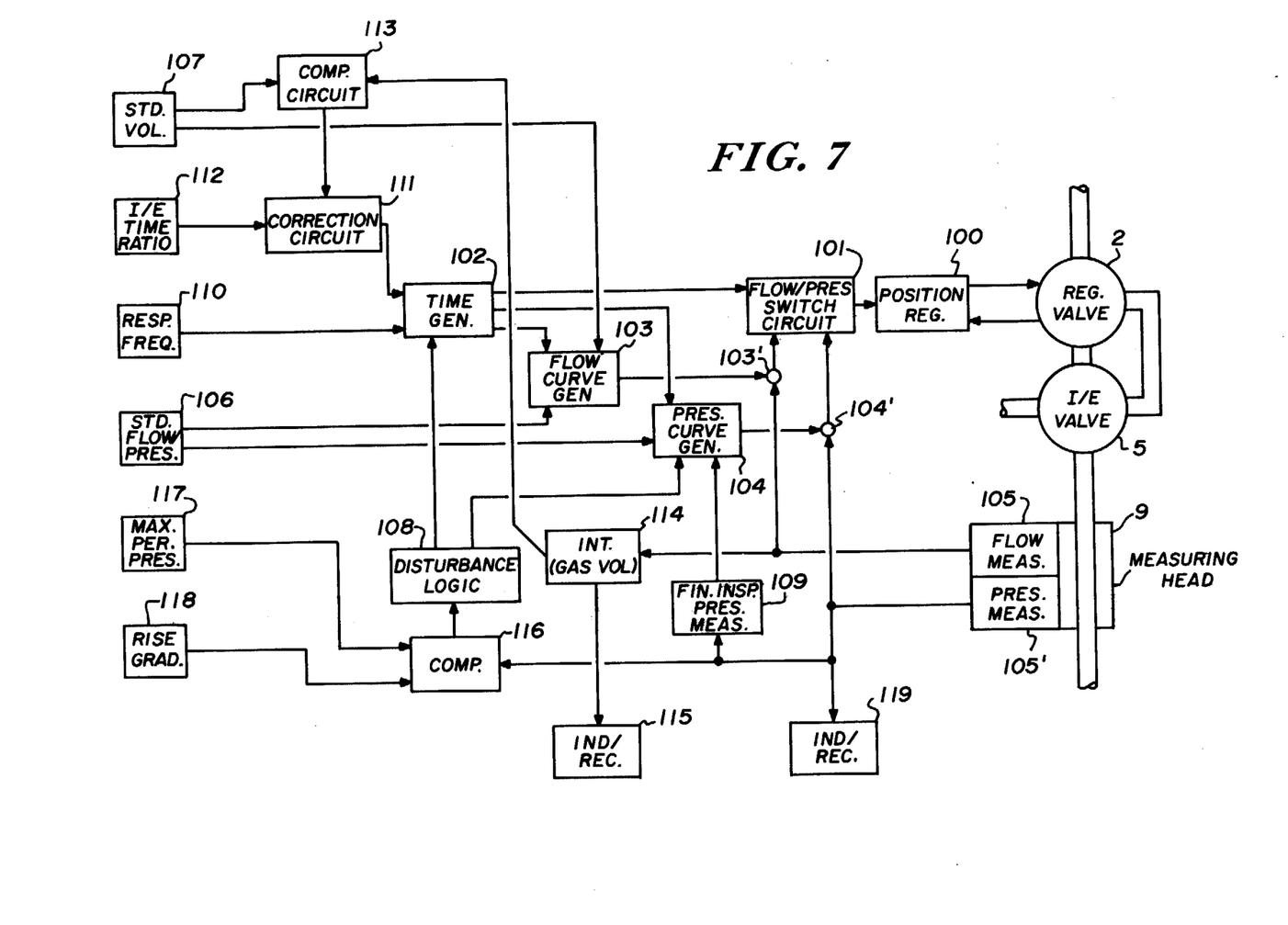
FIG. 7 shows an electrical block diagram of the regulating unit 13.

Construction and function of the regulating unit 13 are visible from FIG. 7 in which a block diagram of this device is shown. In FIG. 7 and in the following description, details of the circuit are not dealt with since the functions represented by blocks can usually be realized as several different types which are familiar to one skilled in the art. Fundamental of the invention is, above all, the combination of the individual functions, especially those of several underlying control loops.

Firstly, there is again visible in the FIG. 7, the control section consisting of regulating valve 2, I/E valve 5 and measuring head 9. The first of the underlying control loops serves for the position regulation of the servomotor 18 of the regulating valve 2. For this purpose the motor 18 is connected with a circuit 100 for the position regulation, abbreviated in the following to position regulator, into which the rotating plate condenser (mounted on the shaft of the motor) of the control device 27 is connected, by which means the loop is closed. The position regulator 100 is connected to a circuit 101 for the switching between flow and pressure regulation, abbreviated in the following to switching circuit. The switching circuit 101 has three inputs, of which the first comes from a time generator 102, which produces by means of given values a chronological operating sequence. The two other inputs of the switching circuit 101 are connected at two adder points 103', 104' with the outputs of two curve generators 103, 104 and with the feed-backs of the flow and pressure control loops. The curve generators produce by means of given values and correction values obtained from within the regulating device, the flow and pressure curves according to which the inspiration and the expiration elapse. The adder points 103', 104' are formed essentially from subtraction circuits in which the measured or actual-signals are subtracted from the standard signals and an error signal is obtained. The loop, consisting of switching circuit 101, position regulator 100, control valve 2, I/E valve 5, flow measuring device 105 and adder point 103', represents the flow control loop.

Appropriately the adder point 104' is connected with the output of the pressure measuring device 105', by which means the pressure control loop is formed.

The standard curve generators 103, 104 have several inputs, of which one each is connected with an external operating element 106, which serves for the adjustment of the desired standard curve. The desired standard curve defines that flow or pressure variation which was obtained without disturbances. If disturbances appear the chosen standard curve is modified accordingly in each case. Each second input of the curve generators 103 and 104 is connected with the time generator 102, from which the conditions for the length in time of a respiration cycle and the ratio of the inspiration to the expiration phase are furnished.

A third input of the flow curve generator 103 is connected with an external operating element 107 for the adjustment of the standard minute volume. The amplitude of the flow curve depends on the choice of the standard minute volume.

A third input of the pressure curve generator 104 is connected with a logic circuit 108 in which disturbances such as spontaneous respiration, coughing, exceeding the maximum pressure or maximum pressure increase, are processed and used for the instigation of certain variations of the course of the respiration cycle. Thus, for example, as already mentioned, the system is switched over to pressure control with an exceeding of the maximum pressure or of the maximum pressure increase during the inspiration. On the other hand the respiration cycle is discontinued in the case of coughing or spontaneous respiration and recommenced at the end of this disturbance. For this purpose a second output of the logic 108 is connected with the time generator 102.

The pressure curve generator 104 has a fourth input, which is connected with a measuring device 109 for the measurement of the final inspiratory pressure. The final inspiratory pressure is delivered therefore to the pressure curve generator 104, because it is used as starting value for the pressure curve to follow during the expiration. In this manner a kink is avoided in the pressure curve, which is extremely undesired. The input of the measuring device 109 is connected to the output of the pressure measuring device 105'.

The time generator 102 has three inputs, of which one, as already mentioned, is connected with the logic 108. A further input is connected with an external operating element 110 for the selection or adjustment of the respiration frequency. The third input of the time generator 102 is connected via a correction circuit 111 with an external operating element 112 for the selection or adjustment of the time ratio between inspiration and expiration. This adjusted ratio is modified accordingly by the correction circuit 111. For this purpose the correction circuit 111 is connected with a comparator circuit 113 for the comparison of the actual gas volume per minute (actual minute volume) supplied to the patient with the adjusted standard minute volume. The actual volume is calculated in an integration circuit 114 from the measured values of the expiratory flow. The expiratory flow was chosen for the calculation because with its employment the effect of a possible leak is readily eliminated. The calculated volume can be supplied via an output 115 to an indicator or recording unit.

The logic circuit 108 is connected with a comparator circuit 116 which carries out a comparison between the actual pressure and the maximum permissible pressure as well as between the rise gradient of the pressure and a corresponding maximum value. The two maximum values for pressure and rise gradient of the pressure are given by the aid of external operating elements 117 and 118. For the determination of the actual values the comparator circuit 116 is connected with the pressure measuring device 105'.

The limitation of the buccal pressure and the rise gradient of rise gradient velocity of the buccal pressure has been provided because too high a pressure or too rapid a pressure rise can give the patient pains. Thus, for example, with rib injuries or similar injuries the maximum values are set as low as possible.

The pressure signal coming from the pressure measuring device 105' is supplied to an indicator or recording unit 119.

As already mentioned, an automatic zero adjustment is provided for the flow and the pressure measurement. The automatic zero adjustment is contained in the flow and pressure measuring devices 105, 105'. For the pressure measurement there has already been described the automatic zero adjustment whose zero adjustment signal is pneumatically obtained. For the flow measurement the zero adjustment is carried out completely electronically. The circuit shown in FIG. 8 which is contained in the flow measuring device 105 serves for this purpose. For the description of the function of this circuit FIG. 9, which reproduces the signals at various points (denoted by a–h) of the circuit, is also taken into consideration.

Figure 8:
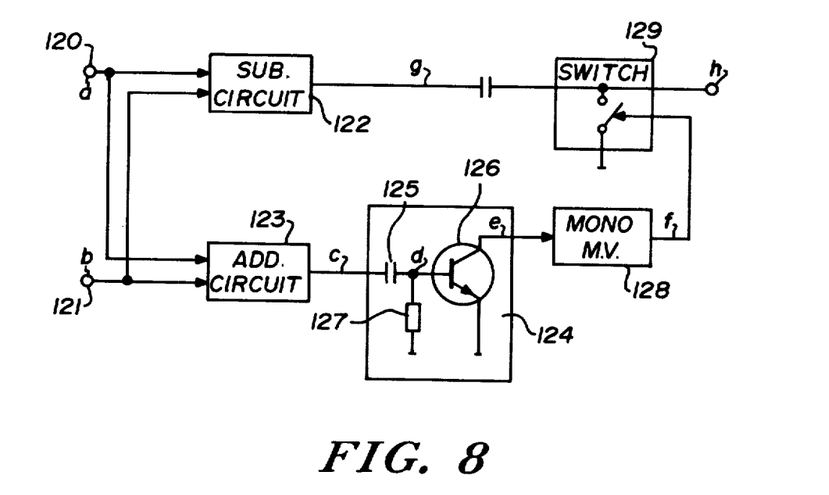
FIG. 8 shows a block diagram of the electrical circuit for the automatic zero adjustment of the flow signal.
Figure 9:
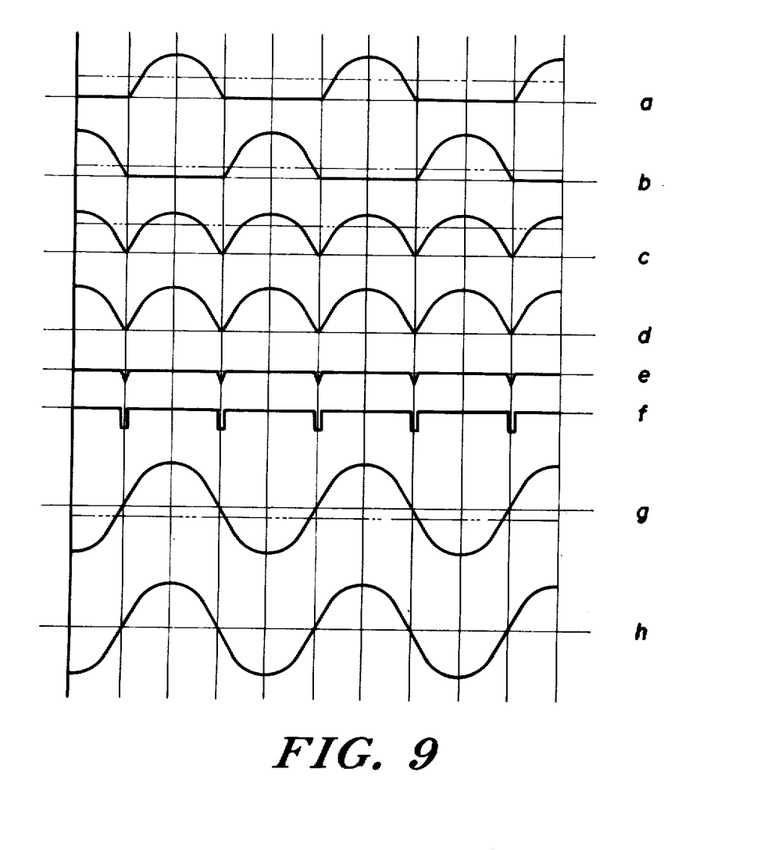
FIG. 9 shows the voltage variation curves at designated points of the circuit shown in FIG. 8.

At the input 120 the signal (a) indicating the inspiratory flow, which comes essentially from the thermistor 62, is obtained. This signal is idealized insofar as during the expiration no pressure variation has been assumed in the measuring point. In reality an amplitude is also produced during the expiration which is however essentially smaller than that during the inspiration. Since the signals, as will be shown subsequently, are subtracted or added, the small amplitudes in the phase not measured in each case are negligible.

There is obtained at the input 121 the signal b indicating the flow variation during expiration, which comes essentially from the thermistor 63 and for which the same is valid as has been stated for the signal a. The two signals a and b have no defined zero lines. From the two inputs 120 and 121 each connection leads to a subtraction circuit 122 and to an addition circuit 123. At the output of the subtraction circuit 122 the signal g is obtained which already substantially represents the flow signal, however has no defined zero line. At the output of the addition circuit 123 the signal c is produced. The output of the addition circuit 123 is connected with an audio link 124.

The input of the audio link is connected via a capacitor 125 with the base of a transistor 126 whose emitter is earthed. A resistor 127 lies between the base of the transistor 126 and earth. In this circuit the signal d is produced at the base of the transistor 126 and the signal e is produced at its collector which represents the output of the audio link. For the improvement of the precision in the present case an operational amplifier with similar functioning is provided.

This signal is supplied to a monostable multivibrator 128 at whose output the signal f is obtained. A switch 129, which momentarily short circuits to earth the signal coming from the subtraction circuit 122 with each change of inspiration phase to expiration phase and vice versa, is actuated essentially by the signal f. At the output of the switch 129 there is obtained therewith the signal h which has by this manner a clearly defined zero line. The output signal h is the signal which is fed back to the input of the control circuit 101 for the purpose of the flow regulation and which is supplied to the integration circuit 114 for the purpose of the volume calculation.

A very large band width is produced by the system of the underlying control loop which is clearly not fully utilized but ensures an increase of the precision in the working range.

We claim;
1. A respirator for automatic regulation of flow and pressure of respiration gas during an inspiration and expiration phase by way of a single conduction path between a source of respiration gas and a patient, comprising:
   a. a single conduction path having a first end adapted to be connected to a source of respiration gas and a second end adapted to be connected to a patient and, in serial arrangement, measuring means forming part of said conduction path for determining the flow and pressure of respiration gas at a single measuring location proximate the said second end and converting the same into electrical signals;
   single first valve means forming part of said conduction path and coupled to the source of respiration gas and adapted to be adjustable between inspiration and expiration positions and for controllably varying the flow and the pressure of the respiration gas during the inspiration phase and expiration phase; and single second valve means forming part of said conduction path for separating inspiratory and expiratory flow, said single second valve means being coupled between said single first valve means and said measuring means said second valve means including an outlet, and means between said first and second valve means for providing fluidic connection of the first valve means to the patient during the inspiration phase when said first valve means is in said inspiratory position and for fluidic connection from the patient to said outlet during the expiration phase when said first valve means is in said expiratory position
   b. electronic regulating means connected with the measuring means and said first valve means for comparing said electrical signals with selected values including standard values of inspiratory and expiratory flows and pressures and for generating a regulating signal indicative of a difference between said selected valves and said electrical signals and thereby controllably adjusting said first valve means for flows and pressures of respiration gas during the inspiratory and expiratory phases.

2. A respirator according to claim 1 wherein the separation between inspiratory and expiratory paths takes place in said conducting line between said first valve means and said single measuring location.

3. A respirator according to claim 1 wherein said measuring means includes
   a curved channel having a first end defining a first axis and a second end defining a second axis, said curved channel being connected via one end thereof to said second valve means and the other end leading to the patient, said curved channel having an outside wall relative to the curve defining a pair of concave bends meeting each other at a center point of the curve, at least two auxiliary channels, designated first and second auxiliary channels, in communication with said curved channel and connected with a pressure gas source for introduction of at least one gas stream into said curved channel, whereby each said auxiliary channel opens into a respective one of said concave bends of said curved channel in the region where an extension of the axis of one of said ends intersects said respective one of said concave bends, and said measuring means further includes thermistor means disposed in each of said auxiliary channels and being electrically coupled to said electronic regulating means.

4. A respirator according to claim 3 wherein said measuring means further includes;

at least third and fourth auxiliary channels disposed for coupling the first and second auxiliary channels and the pressure gas source; and, pneumatic resistor means arranged in the third and fourth auxiliary channels.

5. A respirator according to claim 3 wherein said measuring means further includes pneumatic orifice means disposed in said first and second auxiliary channels relative to said thermistor means such that with each of said first and second auxiliary channels said thermistor means is arranged between the respective end of said curved channel and said pneumatic orifice means.

6. A respirator according to claim 3 wherein said measuring means further includes at least third and fourth auxiliary channels, said third and fourth auxiliary channels opening in the region of the inside wall of the curved channel at locations which are laterally displaced from the curve center in a symmetrical manner and proximate the inside wall, said third and fourth auxiliary channels being connected with said first and second auxiliary channels.

7. A respirator according to claim 6 wherein said measuring means further includes a fifth auxiliary channel connecting the auxiliary channel(s) opening in the region of the inside wall of the curved channel with the atmosphere, said fifth auxiliary channel having at least one thermistor means connected electrically to said regulating means and means for providing a zero adjustment of the measured pressure signal, said fifth auxiliary channel being connected with the pressure gas source.

8. A respirator according to claim 3 wherein said measuring means further includes at least a third auxiliary channel connecting with the atmosphere and said first and second auxiliary channels, said third auxiliary channel including for the purpose of pressure measurement first thermistor means proximate the end thereof opening to the atmosphere and second thermistor means proximate the other end thereof and means for connection with the pressure gas source, said first and second thermistor means being connected with said regulating means.

9. A respirator according to claim 8 wherein said third auxiliary channel includes first pneumatic resistor means arranged between the pressure gas source line and the second thermistor means.

10. A respirator according to claim 9 further including second pneumatic resistor means provided in the line to the pressure gas source.

11. A respirator according to claim 1 wherein said second valve means includes first and second inlet connections and wherein said first valve means comprises a rotary slide valve arrangement which includes:

fixed cylindrical means having first and second borings, leading respectively to said first and second inlet connections of said second valve means, each said boring having an axis lying in a plane perpendicular to the axis of said cylindrical means; and cylinder means, operatively connected to said regulating means, said cylinder means being supported for rotation within said fixed cylindrical means and having an aperture adapted for selective movement into alignment with said first or second borings.

12. A respirator according to claim 11 wherein said first valve means further includes servo-motor means, connected to said regulating means, for providing rotation of said rotatable cylinder means.

13. A respirator according to claim 12 wherein said first valve means further includes means connected to said servo-motor means for adjusting the angular position of the rotatable cylinder means.

14. A respirator according to claim 13 wherein said adjustment means includes rotating plate condenser means.

15. A respirator according to claim 11 further including housing means connected with and enclosing said fixed cylindrical means, and having channels aligned with said first and second borings of said fixed cylindrical means, the channels being coupled to the inlet connections of the second valve means.

16. A respirator according to claim 15 wherein said housing means contains the second valve means and at least a portion of said measuring means.

17. A respirator according to claim 16 wherein said housing means is fabricated of plastic and is disposable.

18. A respirator according to claim 1 wherein said regulating means includes:

circuit means connected with said measuring means and including means for selectively comparing the measured flow and pressure with a respective standard; and switching means connected with said comparing means and said first valve means for controlling said first valve means for flow regulation and pressure regulation in response to said comparing means.

19. A respirator according to claim 18 wherein said comparing means includes:

flow curve generator means, operatively connected to said switching means, for producing a standard curve for the flow variation; and pressure curve generator means, operatively connected to said switching means, for producing a standard curve for the pressure variation.

20. A respirator according to claim 19 wherein said regulating means further includes:

time generator means responsive to the inspiration-expiration time ratio, the respiration frequency and disturbances detected by said measuring means;

a source of normal flow values; and a source of standard minute volume, and wherein said flow curve generator means is connected to said time generator means, said source of normal flow values and said source of standard minute volume.

21. A respirator according to claim 19 wherein said regulating means further includes:
a source of normal pressure values;
time generator means responsive to the inspiration-expiration time ratio, the respiration frequency and disturbances detected by said measuring means; and
means for detecting the preceeding final inspiratory pressure, and wherein said pressure curve generator is connected to said source of normal pressure values, said time generator means, and said means for detecting the preceeding final inspiratory pressure.

22. A respirator according to claim 18 wherein said measuring means includes means for automatic zero adjustment of the measured signal output of said measuring means.

23. A respirator for automatic regulation of the flow and pressure of respiration gas during an inspiration phase and expiration phase and including a connection to a source of respiration gas comprising:
measuring means for determining the flow and pressure of respiration gas and converting the same into electrical signals;
first valve means adjustable for controlling the flow and pressure of respiration gas past said measuring means during inspiration and expiration;
second valve means for separating inspiratory and expiratory flow, and adapted for connection of said first valve means to a patient during the inspiration phase and for connection from the patient to an outlet during the expiration phase, and including a first and second perpendicularly intersecting channels each connected to said first valve means whereby the first channel is also connected to said measuring means and said second channel has an outlet and;
circumfluous body means disposed in said second valve means with the first channel in the region of the intersection; and
electronic regulation means connected with the measuring means and first valve means, for comparing the electrical signals with standard values and for generating a regulating signal for adjusting said first valve means.

24. A respirator according to claim 23 wherein said circumfluous means includes:
conical part means adjacent each side of the cylindrical means and a boring leading from the end of the circumfluous body connected to the measuring means to the exterior surface portion of the circumfluous means opposite the intersection.

25. A respirator according to claim 24 whereby said second valve means includes tube means disposed concentrically to an axis defined by the second channel and opening therein and for connection to said first valve means.

26. A respirator according to claim 24 whereby said circumfluous means includes radial guide vane means on the conical means facing the inlet and twisted with respect to planes intersecting through an axis defined by the first channel.

27. A respirator according to claim 24 whereby the circumflous body central cylindrical means extends in the direction of the inlet from a plane perpendicular to the first channel, set through an axis defined by the second channel.

28. A respirator according to claim 24 whereby the second channel is broadened toward said outlet and serving as a diffuser.

29. A respirator according to claim 24 whereby said second valve means is composed of plastic.

30. A respirator according to claim 29 including: housing means composed of plastic including said second valve means, and part of the first valve means as well as part of the measuring means.

* * * * *